United States Patent
King et al.

(10) Patent No.: US 8,852,139 B2
(45) Date of Patent: Oct. 7, 2014

(54) REVERSIBLE PERISTALTIC PUMP AND OTHER STRUCTURES FOR REFLUX IN EYE SURGERY

(75) Inventors: David King, Pleasanton, CA (US); John I. Muri, Aliso Viejo, CA (US); Thomas B. Sutton, Orange, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 441 days.

(21) Appl. No.: 11/937,640

(22) Filed: Nov. 9, 2007

(65) Prior Publication Data

US 2008/0114290 A1    May 15, 2008

Related U.S. Application Data

(60) Provisional application No. 60/865,163, filed on Nov. 9, 2006.

(51) Int. Cl.
*A61M 1/00* (2006.01)

(52) U.S. Cl.
CPC ........... *A61M 1/0031* (2013.01); *A61M 1/0033* (2013.01); *A61M 2205/12* (2013.01); *A61M 2210/0612* (2013.01); *A61F 9/00745* (2013.01); *A61M 2205/3351* (2013.01); *A61M 1/0058* (2013.01)
USPC ................. 604/28; 604/30; 604/35; 604/118; 604/521

(58) Field of Classification Search
CPC ............ A61F 9/00745; A61M 1/0031; A61M 1/0058; A61M 2001/0033; A61M 2205/12; A61M 2205/3351; A61M 2210/0612
USPC ............... 604/35, 294, 296, 30, 34, 118, 131
See application file for complete search history.

(56) References Cited

U.S. PATENT DOCUMENTS

| | | | | |
|---|---|---|---|---|
| 4,764,165 A * | 8/1988 | Reimels et al. | | 604/35 |
| 5,569,188 A * | 10/1996 | Mackool | | 604/67 |
| 5,649,905 A | 7/1997 | Zanger et al. | | |
| 6,780,166 B2 * | 8/2004 | Kanda et al. | | 604/31 |
| 2001/0023331 A1 * | 9/2001 | Kanda et al. | | 604/43 |
| 2003/0225366 A1 | 12/2003 | Morgan et al. | | |
| 2005/0070859 A1 | 3/2005 | Cull et al. | | |
| 2005/0118048 A1 | 6/2005 | Traxinger | | |
| 2006/0224143 A1 * | 10/2006 | Claus et al. | | 604/521 |

FOREIGN PATENT DOCUMENTS

DE           3713420 A1     11/1988

\* cited by examiner

*Primary Examiner* — Kami A Bosworth
*Assistant Examiner* — Imani Hayman
(74) *Attorney, Agent, or Firm* — Abbott Medical Optics Inc.

(57) ABSTRACT

Devices, systems, and methods for treatment of an eye alter aspiration flow from the eye in response to an occlusion of the aspiration conduit pathway. Where aspiration is drawn from the eye using a volumetric pump, the pump can be reversed so as to induce fluid reflux from the aspiration conduit pathway into the eye to help clear the occlusion. The pump may vary the reverse flow in response to sensed aspiration pressure or the like, and the reverse flow may be halted before the pressure within the aspiration conduit pathway adjacent the eye significantly exceeds the irrigation fluid pressure and/or the pressure within the eye. Reflux may alternatively be generated by modulating a vent valve disposed between an irrigation conduit pathway and the aspiration conduit pathway.

12 Claims, 10 Drawing Sheets

REVERSIBLE PERISTALTIC PUMP AND OTHER STRUCTURES FOR REFLUX IN EYE SURGERY

RELATED APPLICATION

The present application claims priority under 35 U.S.C §119(e) to provisional application No. 60/865,163, filed on Nov. 9, 2006 under the same title. Full Paris Convention priority is hereby expressly reserved.

BACKGROUND OF THE INVENTION

The present invention is generally related to methods, devices, and systems for controlling surgical fluid flows, often during treatments of an eye. In exemplary embodiments, the invention allows clearing of an occlusion in an aspiration conduit pathway during (for example) cataract surgery or the like, optionally by reversing a peristaltic aspiration pump, modulating a vent valve between the aspiration conduit pathway and an irrigation fluid source, or the like.

With age, clouding of the lens or cataracts are fairly common. Cataracts may form in the hard central nucleus of the lens, in the softer peripheral cortical portion of the lens, or at the back of the lens near the capsular bag. Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens and for maintaining the separation between the anterior portion of the eye and the vitreous humor in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms have been used in phacoemulsification and other treatment systems for the eyes, most aspiration flow systems can generally be classified in one of two categories: 1) volumetric-based aspiration flow systems using positive displacement pumps; and 2) vacuum-based aspiration systems using a vacuum source. Among volumetric aspiration systems, peristaltic pumps (which use rotating rollers that press against a flexible tubing to induce flow) are commonly employed. Cassette systems can be used to couple peristaltic pump drive rotors or vacuum systems of the surgical consoles to an eye treatment handpiece, with the flow network conduit of the cassette being disposable to avoid cross-contamination between different patients.

While existing cataract surgery devices, systems, and methods have proven highly effective and have helped numerous patients, still further improvements and refinements remain desirable. For example, both volumetric and vacuum-based aspiration remain (to varying degrees) subject to temporary blockage or occlusion of the aspiration flow. As ultrasound energy breaks up the lens structure within the eye, small and soft tissue particles are readily drawn into an aspiration port of the treatment probe. Unfortunately, larger and/or harder tissue particles may at least temporarily cover the aspiration port of the probe, impeding flow of material and fluids from the eye into the probe. The ultrasound energy transmitted by the probe, in combination with the aspiration pump, often (though not always) eventually break up the occluding particle and successfully withdraw the occlusive material into the probe and from the eye. Unfortunately, significant fluid pressure transients can occur during this process. While existing eye treatment systems have structures that can successfully clear many or all occlusions, known occlusion clearing approaches may actually increase pressure transients, and/or may rely on complex and costly system components. More generally, current occlusion clearing methodologies may have either a relatively slow response time or insufficient pressure control.

In light of the above, it would be advantageous to provide improved devices, systems, and methods for eye surgery. It would be particularly advantageous if these improvements allowed occlusions of an aspiration conduit pathway to be cleared without subjecting the eye to excessive pressure surges, serious underpressurization, or other undesired pressure excursions or transients. It would be particularly advantageous if these improvements could be provided without excessively increasing the complexity, cost, or difficulty in using these sophisticated eye treatment systems.

BRIEF SUMMARY OF THE INVENTION

The present invention generally provides improved devices, systems, and methods for treatment of an eye. Exemplary embodiments allow alteration of an aspiration flow in response to a request by the user and/or an occlusion of the aspiration conduit pathway. In some embodiments, most often (though not necessarily) where aspiration is drawn from the eye using a volumetric pump, the pump is reversed so as to provide venting of the aspiration conduit pathway or induce fluid reflux from the aspiration conduit pathway into the eye to help clear the occlusion. The reversing of the pump may be halted before the static pressure within the aspiration conduit pathway reaches a predetermined value. For example, sufficient reflux may be induced to clear occlusions, with the reflux being produced at least in part from the momentum of fluid within the aspiration conduit pathway toward the eye. In other embodiments, reflux may be generated by continuing to drive a volumetric pump in the reverse direction, by modulating a vent valve disposed between an irrigation conduit pathway and the aspiration conduit pathway, or the like.

In a first aspect, the invention provides an eye treatment method comprising directing an irrigation flow into the eye through an irrigation conduit pathway. Material is aspirated from within the eye by drawing an aspiration flow through an aspiration conduit pathway with a pump. In response to a user request and/or an occlusion of the aspiration flow, the pump is reversed and fluid is pumped back into the aspiration conduit pathway, for example, to reflux flow into the eye to help clear the occlusion.

Optionally, the pump may comprise a volumetric pump such as a peristaltic pump or the like. The occlusion may induce a compliant reduction in volume of the aspiration conduit pathway between the eye and the pump. Reversing the pump may at least partially compensate for the reduction in volume, allowing the aspiration conduit pathway to return back toward its pre-occlusion size. The pump speed may be modified in response to a variation in pressure along the aspiration conduit pathway between the pump and the eye, and/or to another aspiration parameter or characteristic. Reversing of the pump may be halted when a pressure of the aspiration flow adjacent the eye is less than or substantially equal to an irrigation flow pressure at the eye so that the reflux into the eye is largely generated by momentum of the aspiration conduit pathway toward the eye. The reflux may be primarily generated by the momentum, and in some embodiments may be entirely generated by the momentum, rather than relying on any reflux-inducing static pressure differential between the pump-generated pressure and the pressure within the eye.

In many embodiments, a substantially constant reverse pumping flow rate or pump speed may be maintained while the absolute pressure of an aspiration conduit is below a threshold. In other embodiments, the reverse pumping flow rate or speed may vary as a particular function of a system parameter while the absolute pressure of an aspiration conduit is below a threshold. For example, when an aspiration line pressure is between zero and a first threshold, the flow rate or pump speed may be constant or determined using a first linear relationship between flow rate (or pump speed) and line pressure. A second linear relationship may be applied when the line pressure is between the first threshold and a second threshold (e.g., atmospheric pressure). A third linear relationship may be applied when the line pressure is between the second threshold and a third threshold (e.g., between atmospheric pressure and an irrigation bottle pressure). Further thresholds may be employed to further segment the value of the flow rate or pump speed. Also, one or more of the linear relationships may be replaced by non-linear relationships between the pumping flow rate (or pump speed) and a system parameter such as aspiration line pressure. Other system parameters may include an irrigation pressure, a temperature, and the like.

The irrigation and aspiration flows may be initiated by actuation of a foot pedal input device. For example, irrigation flow may be initiated by movement of the foot pedal from a nominal undeflected position to a first position. Aspiration flow may be added to the irrigation flow by moving the foot pedal from the first position to a second position. Energizing of a probe through which the aspiration flow is withdrawn from the eye may be added by moving the pedal from the second position to a third position. A surgeon or other system user may release the pedal, allowing it to return to the nominal position, when the occlusion of the probe is recognized, and the pump may be reversed while the foot pedal is in the nominal position. In other embodiments, the system may initiate reversal of the pump and reflux, or the surgeon may input a command to initiate reflux without returning the foot pedal to the nominal position.

The reversing of the pump may be controlled in response to a change or rate of change of aspiration pressure, a pressure of the irrigation flow, a height of the eye of the patient, and/or the like. The height of the eye of the patient may be estimated from the height of an accessory tray of the system (the tray normally being at or near the patient's eye level). The pressure of the irrigation flow may be related to a height of an irrigation fluid container, and the height of the irrigation container may be driven and/or sensed by a controller.

In some embodiments, a vacuum source may be coupled to the aspiration fluid conduit by an aspiration selector valve, for example, so that aspiration flow may be induced by either the vacuum source or the volumetric pump. The aspiration selector valve will typically be partially or completely closed (so that the vacuum source does not affect pressure within the aspiration conduit pathway) during reversing of the pump.

In another aspect, the invention provides an eye treatment method comprising directing an irrigation flow into the eye through an irrigation conduit pathway. Material is aspirated from within the eye by drawing an aspiration flow through an aspiration conduit pathway. In response to an occlusion of the aspiration flow (the occlusion typically inducing a compliant reduction in volume of the aspiration conduit pathway), fluid may be introduced into the aspiration conduit pathway. The introduction of fluid into the aspiration conduit pathway may be controlled in response to a pressure along the aspiration conduit pathway so that a maximum reflux pressure within the aspiration conduit pathway adjacent the eye is less than, or substantially equal to, an irrigation flow pressure adjacent the eye or some other predetermined pressure. As a result, reflux into the eye is generated at least in part by momentum in the aspiration conduit pathway toward the eye.

The material may be aspirated from the eye using a peristaltic (or other volumetric) pump, and the fluid may be introduced into the aspiration conduit pathway by reversing the peristaltic pump. In other embodiments, the material may be aspirated from the eye using a vacuum source such as vacuum pump (optionally being a Venturi pump, a rotary vane pump, or the like). The fluid may be introduced into the aspiration conduit pathway by opening a valve between the irrigation conduit pathway and the aspiration conduit pathway. Alternatively, another higher pressure source my be used in place of the irrigation pathway, for example the high pressure side of the aspiration pump. The introduction of the fluid may be controlled by modulating the valve in response to the pressure along the aspiration conduit pathway, so that the valve provides a varying flow resistance.

In another aspect, the invention provides an eye treatment system comprising an eye treatment probe and an eye treatment console having a processor and an aspiration pump drive. A cassette couples the probe to the processor and/or console. The cassette has a pressure sensor disposed along an irrigation conduit pathway for determining an irrigation flow pressure into the eye via the probe. The cassette and probe have an aspiration conduit pathway coupled to the pump for aspirating material from within the eye. The processor of the console is configured to reverse the pump to reflux fluid from the aspiration conduit pathway and into the eye to help clear occlusions.

In another aspect, the invention provides an eye treatment system comprising an irrigation conduit pathway for directing an irrigation flow into the eye. An aspiration conduit pathway aspirates material from within the eye. The aspiration conduit pathway is subject to a compliant reduction in volume induced by an occlusion of the aspiration flow. A pressure sensor is coupled to the aspiration conduit pathway for transmitting a pressure therefrom. A controller is coupled to the aspiration conduit pathway. The controller is configured to effect introduction of fluid into the aspiration conduit pathway in response to the pressure, so that a maximum reflux pressure within the aspiration conduit pathway adjacent the eye is less than or substantially equal to a predetermined pressure, for example, the irrigation flow pressure adjacent the eye. Hence, reflux into the eye may be generated at least in part by momentum in the aspiration conduit pathway toward the eye.

DETAILED DESCRIPTION OF THE INVENTION

The present invention generally provides improved devices, systems, and methods for treating an eye of a patient. Exemplary embodiments provide improved techniques for directing fluids into an aspiration conduit pathway between an eye and an eye treatment console for clearing occlusions and the like, particularly during treatments within an interior of the eye.

In many embodiments, an eye treatment probe handpiece will be coupled to an eye treatment console by a cassette mounted to the console. The cassette may include a surgical fluid network, typically including an irrigation conduit pathway for directing irrigation fluid toward the eye and an aspiration conduit pathway for directing material (typically including both fluid and tissue) from the eye. The fluid network of the cassette may include resiliently deformable tubing, flexible (but less compressible or expandable) tubing, a pressure sensing mechanism, a holding tank or chamber, and/or the like. The cassette and console may use a volumetric pump to aspirate the material from within the eye through the aspiration conduit pathway. Other embodiments may employ a vacuum source such as a vacuum pump (optionally being a Venturi pump or a rotary vane pump) or a connector for attachment to a vacuum system of the operating room. Exemplary embodiments may optionally include both a volumetric peristaltic pump and a vacuum source, with the operator or computer controller selecting between the aspiration drive mechanisms. Regardless, the cassette will often comprise a disposable structure that separates the surgical fluids from more expensive and reusable components of the console. Other embodiments may include a reusable cassette body and disposable or sterilizable tubing.

Figure 1:
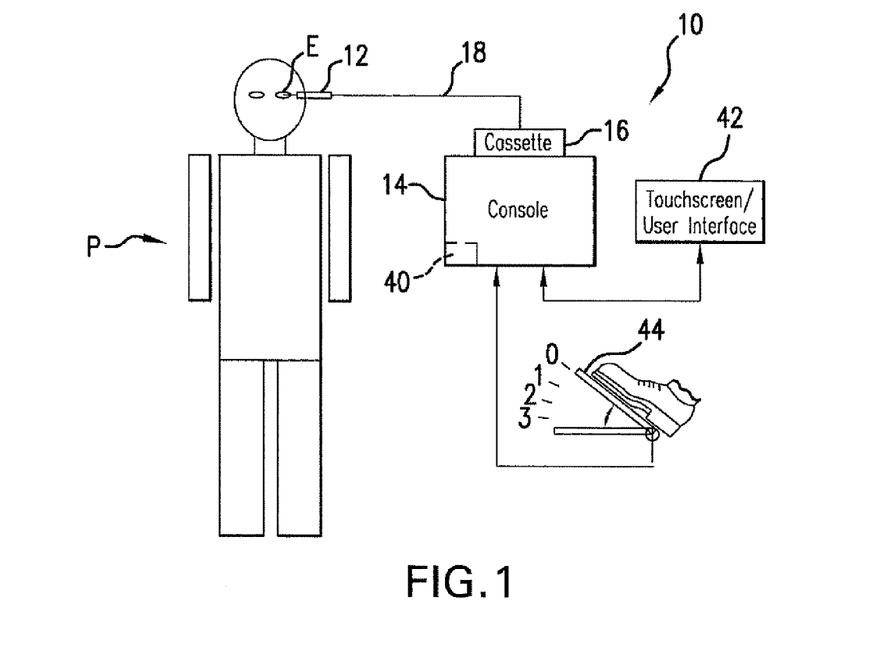
FIG. 1 schematically illustrates an eye treatment system in which a cassette couples an eye treatment probe with an eye treatment console, along with a method for use of the system for treating the eye of a patient.

Referring now to FIG. 1, a system 10 for treating an eye E of a patient P generally includes an eye treatment probe handpiece 12 coupled to a console 14 by a cassette 16. Handpiece 12 generally includes a handle for manually manipulating and supporting a probe tip. The probe tip has a distal end which is insertable into the eye, with one or more lumens in the probe tip allowing irrigation fluid to flow into the eye. Aspiration fluid may also be withdrawn through a lumen of the probe tip, with the console generally including a vacuum aspiration source, a volumetric aspiration pump, or both. Flexible conduits 18 of the cassette 16 help avoid direct contact between irrigation and aspiration fluids flowing to or from the eye and the components of the console 14.

When the distal end of the probe tip of handpiece 12 is inserted into an eye E (for example) for removal of a lens of a patient with cataracts, an electrical conductor (not shown) may supply energy from console 14 to an ultrasound transmitter of the handpiece. This ultrasound energy helps to fragment the tissue of the lens, which can then be drawn into a port of the tip by aspiration flow. Alternatively, the handpiece may be configured as a vitrectomy probe or an irrigation/aspiration (I/A) probe. So as to balance the volume of material removed by the aspiration flow, an irrigation flow through handpiece 12 (or a separate probe structure) may be provided, with both the aspiration and irrigation flows being controlled by a controller 40 of console 14. In other embodiments, the handpiece 12 may be configured to remove vitreous material in the posterior chamber of the eye E, for example, by including an electrically or pneumatically driven cutter blade.

Controller 40 may include an embedded microcontroller and/or many of the components of a personal computer, such as a data bus, a memory, input and/or output devices (including a touchscreen user interface 42 and a foot pedal input device 44), and the like. Controller will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 40 may have (or be coupled to) a recording media reader, or the code may be transmitted to controller 40 by a network connection such as an internet, an intranet, an Ethernet™, a wireless network, or the like. Along with programming code, controller 40 may include stored data or correlations for implementing the methods described herein, and may generate and/or store data that records parameters corresponding to the treatment of one or more patients. Many components of console 14 may be found in or modified from known commercial phacoemulsification systems from Advanced Medical Optics Inc. of Santa Ana, Calif.; Alcon Manufacturing, Ltd. of Fort Worth, Tex.; Bausch and Lomb of Rochester, N.Y., and other suppliers.

Figure 1A:
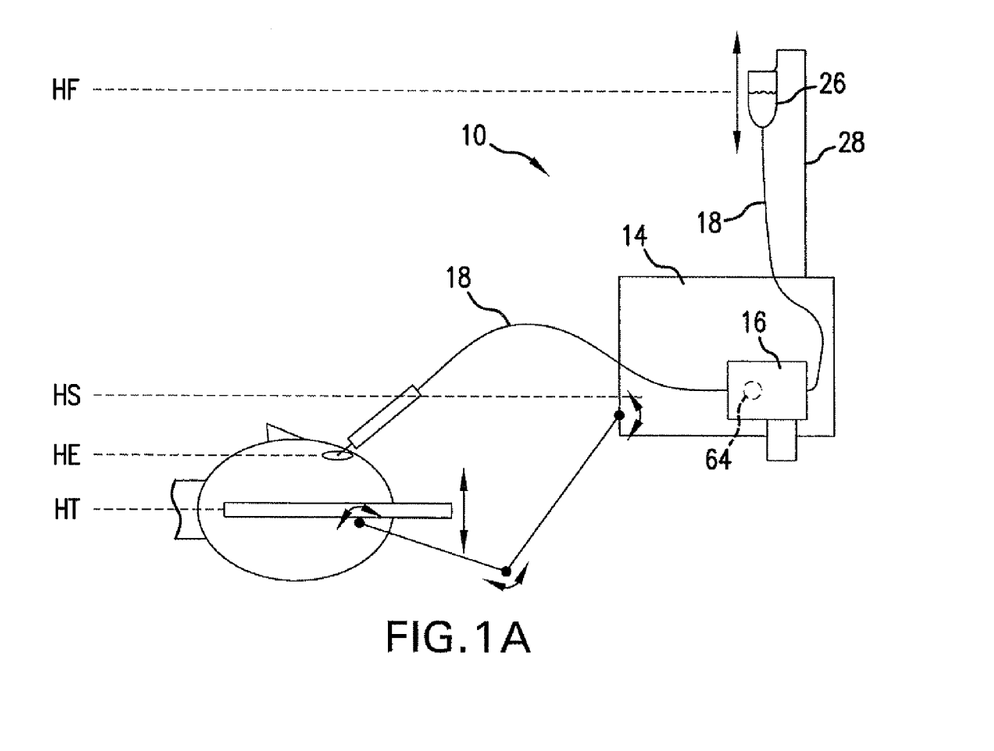
FIG. 1A is a schematic side view of a method of treating an eye using the system of FIG. 1, showing the differing heights of various components of the treatment system and their effect on pressures of the surgical fluids.

Referring now to FIG. 1A, accurate surgical fluid flows into and/or out of eye E from system 10 will often benefit from information regarding pressures within the aspiration and/or irrigation conduit pathways. In general, a pressure sensor 64 may generate signals indicating pressure within the aspiration conduit pathway. The processor of console 14 may make use of the pressure signals from sensor 64 to drive an aspiration pump, and the like.

While the pressure measured by sensor 64 is adequate for many purposes, the pressure within the aspiration conduit pathway defined by the probe tip lumen and other structures of handpiece 12, by flexible tubing 18, and/or by the other fluid network elements of cassette 16 at locations different than that of pressure sensor 64 may also be of interest. For example, it may be beneficial to determine a pressure within the aspiration conduit pathway adjacent eye E. As eye E may generally be at a height HE that is different than the height of the sensor HS, the pressure within the aspiration conduit pathway adjacent eye E may be determined at least in part from the pressure head or height differential between the height of the eye HE and the height of the sensor HS.

A wide variety of structures and techniques may be used to measure the height of the eye HE, including providing appropriate sensors in (or coupled to) handpiece 12, by determining a height of the operating table or other patient support structure, or the like. As the height of the eye HE may differ for different patients and different system users, console 14 may include an input for receiving some information regarding the height of the eye, such as by the system user inputting an estimated height of the eye, a sensor used to measure the height of a structure that may be at least partially associated with a height of the eye, or the like. In the exemplary embodiment, the processor of console 14 may estimate a height of the eye HE from the height HT of an accessory tray 22.

Accessory tray 22 may be supported by an articulatable linkage 24, with one or more joints of the linkage having a sensor coupled to the processor of console 14. Accessory tray 22 generally holds tools and/or medication used during treatment of eye E, and is flexibly moved by articulating linkage 24 so that tray 22 is near the eye. There may be some slight offset in height between the height of the tray HT and the height of the eye HE, the tray optionally being at or slightly below the eye for convenient access to the contents of the tray without blocking access to eye E during the use of handpiece 12. Typically, the height of the tray HT is between about 0 and 8 inches below the height of the sensor HS, depending on the structure of tray 22, the use and structure of handpiece 12, physician preferences, and the like. A standard offset may be applied by processor 40 of console 14 (see FIG. 1), individual offsets may be applied for particular surgeons or system users, and/or the system user may input a measured or estimated difference in height between tray 22 and eye E for each procedure on a particular patient or eye. In some embodiments, aspiration and/or irrigation pressure heads may be determined by processor 40 based on an assumption that the eye height HE is at or above the tray height HT. For example, to be conservative the eye may simply be assumed to be at the lowest tray level within the range of movement of the tray, such as 8 inches below the height of the sensor HS. Regardless, the processor of console 14 may make use of the sensed height HT of tray 22 to determine a head pressure differential between the measured pressure 64 and the pressure within aspiration conduit pathway adjacent eye E.

Still referring to FIG. 1A, differential head pressures may also be used by the processor of console 14 to determine an irrigation pressure within an irrigation conduit pathway adjacent eye E. An irrigation container 26 is supported at an irrigation fluid height HF, with the height of the irrigation fluid varying with a height of a fluid support 28. The fluid support 28 may have a sensor to indicate the height of the fluid HF to the system processor of console 14, and/or fluid support 28 may be driven by an actuator to vary the height of the fluid and hence the irrigation fluid pressure within the irrigation conduit pathway adjacent eye E. The processor 40 may determine the irrigation fluid pressure adjacent eye E from the difference in height between the fluid height HF and the height of the eye HE based on the height of the tray HT and any offsets between the tray and eye.

Figure 2A:
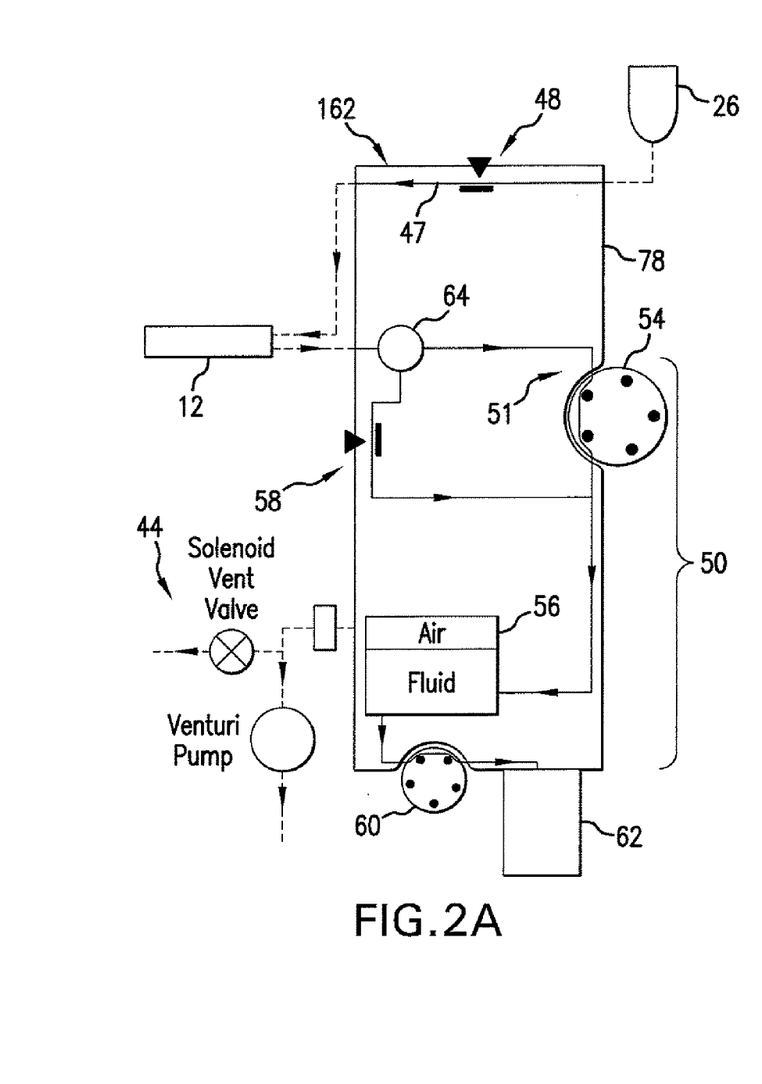
FIGS. 2A and 2B illustrate alternative cassettes having surgical fluid pathway networks for use in the system of FIG. 1.

Referring now to FIG. 2A, elements included in the aspiration and irrigation fluid flow network of an eye treatment system employing a first exemplary cassette 16a are shown. As described above, irrigation source 46 typically provides irrigation fluid pressure by relying at least in part on a gravity pressure head that varies with a height of an irrigation container 26 (see FIG. 1A) or the like. An irrigation on/off pinch valve 48 may include a short segment of a resilient flexible conduit of cassette 16b, which can be engaged and actuated by an actuator of the console. A surface of a cassette body 78 may be disposed opposite the actuator to facilitate closure of the conduit lumen. Alternative irrigation flow systems might include volumetric pumps, alternative fluid pressurization drive systems, fluid pressure or flow modulating valves, and/or the like. Regardless, the irrigation network generally defines an irrigation fluid conduit path 47 between irrigation source 46 and an irrigation port on the insertable probe tip of handpiece 12.

In cassette 16a, an aspiration flow network 50 generally provides an aspiration flow path that can couple an aspiration port in the probe tip of handpiece 12 to either a peristaltic pump 54 and/or a holding tank 56. Fluid aspirated through the handpiece may be contained in holding tank 56 regardless of whether the aspiration flow is induced by peristaltic pump 54 or the vacuum applied to the holding tank. When valve 58 is closed and peristaltic pump 54 is in operation, pumping of the aspiration flow may generally be effected directly by the peristaltic pump, independent of the pressure in the holding tank 56. Conversely, when peristaltic pump 54 is off, flow through the peristaltic pump may be halted by pinching of the elastomeric tubing of the peristaltic pump by the rotors of the peristaltic pump drive of the console. Regardless, the pressure within tank 56 may be maintained at a controlled vacuum level, often at a fixed vacuum level, by a vacuum pump system 44 of the console. Aspiration flow that drains into tank 56 may be intermittently removed by peristaltic drain pump 60 and directed to a disposal fluid collection bag 62.

The operation of aspiration flow network 50 may be understood by first considering the aspiration conduit pathway 51 when valve 58 is closed. In this mode, peristaltic pump 54 draws fluid directly from handpiece 12, with a volumetric peristaltic pump flow rate being controlled by the system controller. To determine the appropriate flow rate, the level of vacuum within the aspiration flow network may be identified using vacuum sensor 64 disposed along the effective aspiration conduit pathway between peristaltic pump 54 and the aspiration port of handpiece 12. While the aspiration material flows through holding tank 56 and eventually into control bag 62, the holding tank pressure may have little or no effect on the flow from the handpiece in this mode.

When peristaltic pump 54 is not in operation, rotation of the peristaltic pump is inhibited and the rotors of the peristaltic pump pinch the arcuate resilient tubing of the pump so as to block aspiration flow. Material may then be drawn into the aspiration port of handpiece 12 by opening selector valve 58. When valve 58 is open, the aspiration port draws fluid therein based on the pressure differential between holding tank 56 and the chamber of the eye in which the fluid port is disposed, with the pressure differential being reduced by the total pressure loss of the aspiration flow along the aspiration path between the tank and port. Regardless, cassette 16a allows the eye treatment system to operate in either peristaltic or vacuum-based pumping modes.

Figure 2B:
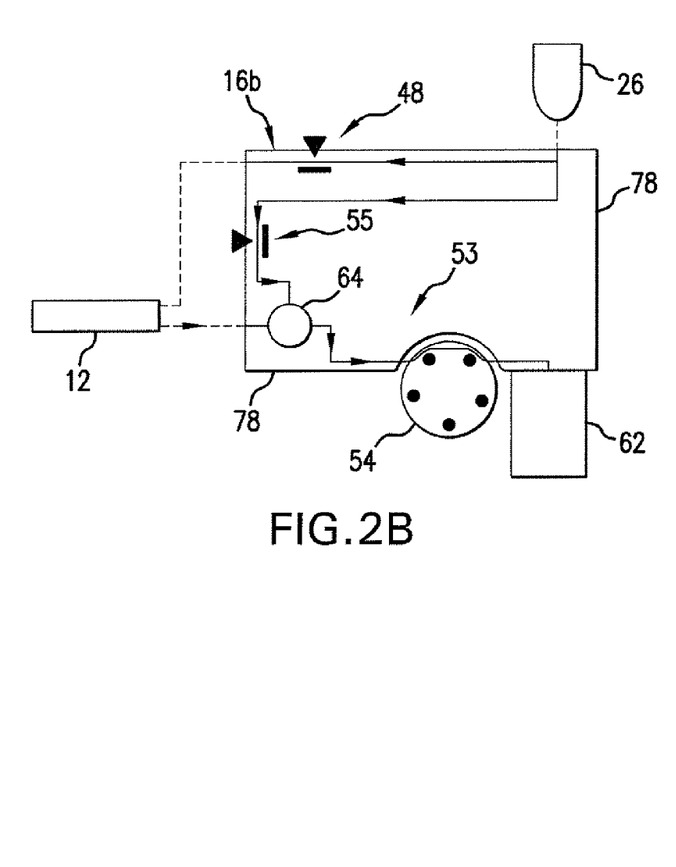

Referring now to FIG. 2B, in some embodiments a system user will perform treatments which may only employ peristaltic pumping. Hence, alternative cassette 16b includes a somewhat simpler aspiration flow network having a single aspiration conduit pathway 53 coupling an aspiration port of handpiece 12 to peristaltic pump 54. Hence, alternative cassette 16b may operate in a manner similar to that described above regarding the use of cassette 16a when selector valve 58 is closed, with the exception that the aspiration fluid downstream of the peristaltic pump 54 is transmitted directly to collection bag 62 (rather than via holding tank 56). In some embodiments of these structures and methods, a vacuum source alone may be used to drive aspiration flow.

Regardless of whether the volumetric and/or vacuum pump capabilities of cassette 16a are available, or whether only volumetric pumping is available through alternative cassette 16b, the aspiration port or ports of handpiece 12, and/or the aspiration conduit network downstream of the port(s) may occasionally become occluded during use. When using volumetric pumping, occlusion of the aspiration conduit pathway while peristaltic pump 54 is turning results in a reduction in pressure along the aspiration conduit pathway between the occlusion and pump, which can often be detected at vacuum sensor 64. Some of the tubing along the pathway may be resilient tubing to facilitate closure of pinch valves and the like. Other portions of the aspiration conduit pathway may be defined by flexible tubing which is somewhat stiffer in cross-section so as to limit the change in volume of the aspiration conduit pathway induced by an occlusion. Nonetheless, the pressure reduction caused by the occlusion will typically cause some, and often a significant, change in the total volume of the aspiration conduit pathway.

In many cases, application of ultrasound energy by the probe tip will relatively quickly clear an occlusion with little or no action taken by the surgeon or other system operator. The controller of the console may vary the peristaltic pumping speed in response to a change in sensed vacuum level in such cases, where the occlusion may clear quickly enough that no operating changes are required. However, other occlusions may continue to block the aspiration flow even after the peristaltic pump 54 is completely halted, and/or after the system user inputs a command to halt aspiration flow.

As schematically illustrated in FIG. 1, operation of system 10 and handpiece 12 may, at least in part, be controlled using foot pedal 44. For example, no surgical fluid flows or energy may be delivered to the probe when foot pedal 44 is in a nominal or zero position. When the system operator presses foot pedal 44 to a first position 1, irrigation flow may be commenced by opening of the irrigation pinch valve. Aspiration flow may be added to the irrigation flow by positioning the foot pedal 44 at a second position 2, with the application of ultrasound energy to the probe tip being added at foot position 3. When the system user determines that flow through the aspiration conduit pathway has been occluded and does not appear to be opening in a reasonable amount of time despite the application of ultrasound energy, foot pedal 44 may be returned to its nominal position zero to temporarily halt the treatment of eye E while the occlusion is cleared.

Referring again to FIGS. 2A and 2B, various venting and reflux approaches may be used in connection with the systems described herein to help clear occlusions and the like. At least two different approaches may be applied to clear occlusions: venting of the aspiration system and reflux. Venting generally refers to introduction of fluids into the aspiration conduit pathway so as to decrease a level of vacuum within the conduit pathway (e.g., increase the absolute pressure within the aspiration conduit pathway) without refluxing material into the eye. Such a reduction of the vacuum may help allow oversize tissue fragments to be cleared from an outer surface of the probe tip. Reflux refers to causing fluid from within the aspiration conduit pathway to flow through the aspiration port(s) and into the eye (or other environment surrounding the aspiration port when the aspiration occurs), optionally by introduction of fluid into the pathway. Reflux may help clear obstructions from over the outer surface of the probe tip, obstructions wedged or otherwise disposed at least partially within the aspiration port, and/or obstructions or occlusive material which has entered into the aspiration conduit pathway by expelling the occlusions from the probe. While they can be related and in some embodiments may be combined, venting may be employed without inducing reflux.

Various venting and reflux methodologies may be used during ophthalmic surgical procedures, particularly those procedures which make use of pumps for aspiration of material from the eye (including volumetric pumps such as a peristaltic pump, vacuum pumps such as a Venturi pump or rotary vane pump, and the like). Preferred methodologies will often have both a relatively fast response time and allow accurate control over the pressures and/or flows within the aspiration conduit pathway.

Referring once again to FIG. 2B, venting and/or aspiration may optionally be provided using an irrigation vent valve 55. The aspiration conduit pathway may be vented using such a vent valve, with the vent valve optionally providing fluid communication between the aspiration conduit pathway and a source of fluid at a higher pressure than that of the aspiration line, such as the irrigation conduit pathway 47. In alternative embodiments, venting may be provided to the atmosphere or the like, although venting to the irrigation line may provide a faster response due to the enhanced pressure of the irrigation flow. Venting to the higher pressure irrigation fluid may enhance response time, though may also benefit from additional care to provide adequate pressure control within the aspiration conduit pathway during venting. In exemplary venting systems relying on a vent valve to irrigation flow, atmospheric pressure, and/or the like, irrigation vent valve 55 will preferably allow both on/off control of the venting flow into the aspiration conduit pathway, together with venting modulation control to vary the venting flow in response to signals from vacuum sensor 64. While use of a vent valve that allows modulation provides a relatively simple mechanical structure for cassette 16b, accurate modulation of vent flow into the aspiration conduit pathway to provide both good response time and accurate control may involve calibration of the vent valve properties, replacement of a simple standard pinch valve arrangement with a modified structure (for example, having an elongate actuator surface engaging a significant length of flexible vent conduit tubing along the direction of venting flow to provide repeatable and reliable throttling), and/or the like.

Alternative venting and/or reflux methodologies may employ the structure of peristaltic pump 54 to introduce fluid into the aspiration conduit pathway and/or to induce reflux from the port of the handpiece probe tip. Venting and/or reflux may be provided by reversing the direction of rotation of the peristaltic pump from its normal operation. This reversal of the peristaltic pump may cause fluid to be controllably introduced into the aspiration conduit pathway and toward handpiece 12. By controlling both the direction and rate of rotation of the pump, the pressure in the aspiration line may be precisely controlled, often with a feedback from vacuum sensor 64. In addition, the pump and associated electronic controller of the console can be configured to provide an advantageously fast response time. In some embodiments, by using the existing peristaltic pump for venting and/or reflux, a valve that might otherwise be included for venting of the aspiration line may either be used for other purposes or eliminated altogether, as can be understood with reference to FIGS. 2A and 2B. Hence, the cassette body 78 of cassette 16a (shown in FIG. 2A) may be configured by mounting of appropriate fluid network elements thereon for use with vacuum and/or peristaltic pumps, or as shown in FIG. 2B as alternative cassette 16b when relying only on a peristaltic pump for aspiration. Console 14 may make use of the same two pinch valve actuation structures for use either as a selector valve 58 or an irrigation vent valve 55, depending on the configuration of the cassette. In some embodiments, a combination venting system may be employed in which reversal of the peristaltic pump is combined with opening and/or modulation of an irrigation vent valve 55.

When relying on peristaltic pump 54 to provide venting and/or reflux in cassette 16a or alternative cassette 16b, venting and/or reflux may generally be provided by rotating the pump head in an opposite direction (e.g., counterclockwise in FIG. 2A). As will be described below with reference to FIGS. 7A and 7B, exemplary embodiments may effect reflux from the probe tip without pumping sufficient fluid into the aspiration vent line so that the aspiration conduit pathway adjacent the port has a higher static pressure than an irrigation pressure and/or fluid pressure generally within eye E. As it may be advantageous to avoid inducing excessive reflux into the eye and overpressurizing the eye, reflux may be induced by the momentum of fluid vented into the aspiration conduit pathway, and by halting flow into the aspiration conduit pathway when the signals from vacuum sensor 64 indicate that the pressure of the aspiration fluid adjacent the eye (when the differential head pressure is accounted for between the height of the eye and the height of the pressure sensor) is substantially equal to or less than the irrigation pressure at the eye (and hence the pressure within the eye itself). While the pressure of the aspiration conduit pathway adjacent the eye that is induced may be less than, equal to, or very slightly greater than the pressure within the eye, the pressure will remain substantially equal to or less than the pressure within the eye so long as reflux flow is induced largely by the momentum of fluid within the aspiration conduit pathway (rather than being induced by a positive pressure differential). In certain embodiments, reflux may be primarily induced by the momentum, with some embodiments being induced solely by the momentum.

While the reflux described herein will often be generated by reversal of peristaltic pump 54 and/or modulation of irrigation vent valve 55, still further alternative venting and/or reflux methodologies may be used to induce the momentum-induced reflux described herein. For example, the entire pump head of peristaltic pump 54 could be translated, with the pump head shown in FIGS. 2A and 2B being moved to the left in order to move fluid back toward the handpiece.

Figure 3:
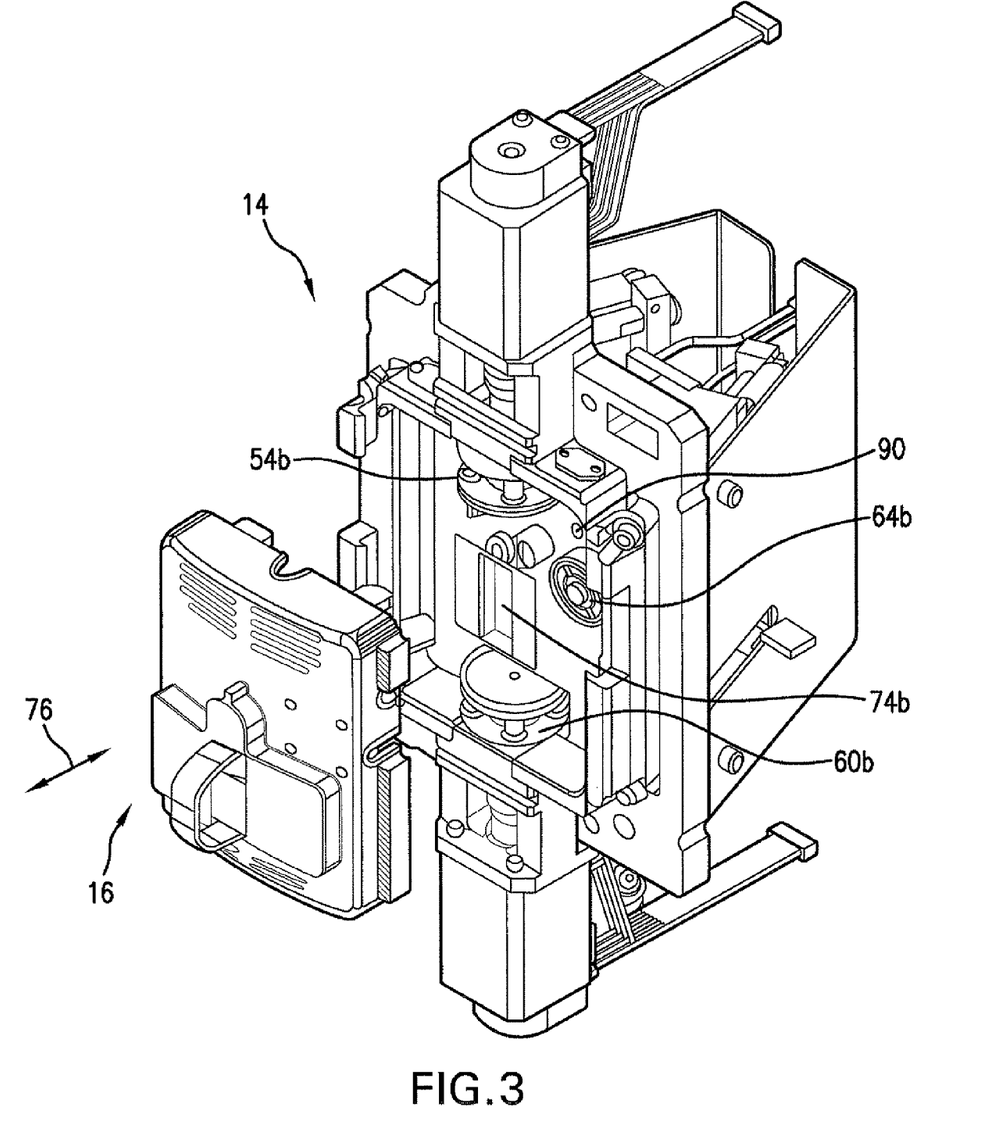
FIG. 3 is a perspective view showing an exemplary embodiment of an eye treatment cassette and the receptacle of the console for mounting the cassette, along with associated components of the console.

Exemplary cassette, receptacle, and fluid network structures are illustrated in FIGS. 3-6. Referring first to FIG. 3, in the exemplary embodiment cassette 16 can be advanced along a mounting axis 76 while the cassette is manually supported until the surfaces of the cassette body engage receptacle surfaces of console 14. C-shaped channels define at least a portion of the receptacle, and can be driven to automatically draw the cassette 16 into a fully mounted position on console 14 along mounting axis 76. Automated mounting may be actuated by a microswitch 90, and helps provide the desirable engagement forces between the peristaltic pump rotor 54b, a peristaltic pump rotor 54b, a peristaltic pump drain rotor 60b, and other components of the console with the corresponding fluid network elements of cassette 16. A pressure detection surface 64b is also seen in FIG. 3, with the detecting surface engaging a surface of the pressure sensor of the console so as to transmit a signal to the processor of console 14 indicating the pressure along the aspiration conduit pathway.

Figure 3A:
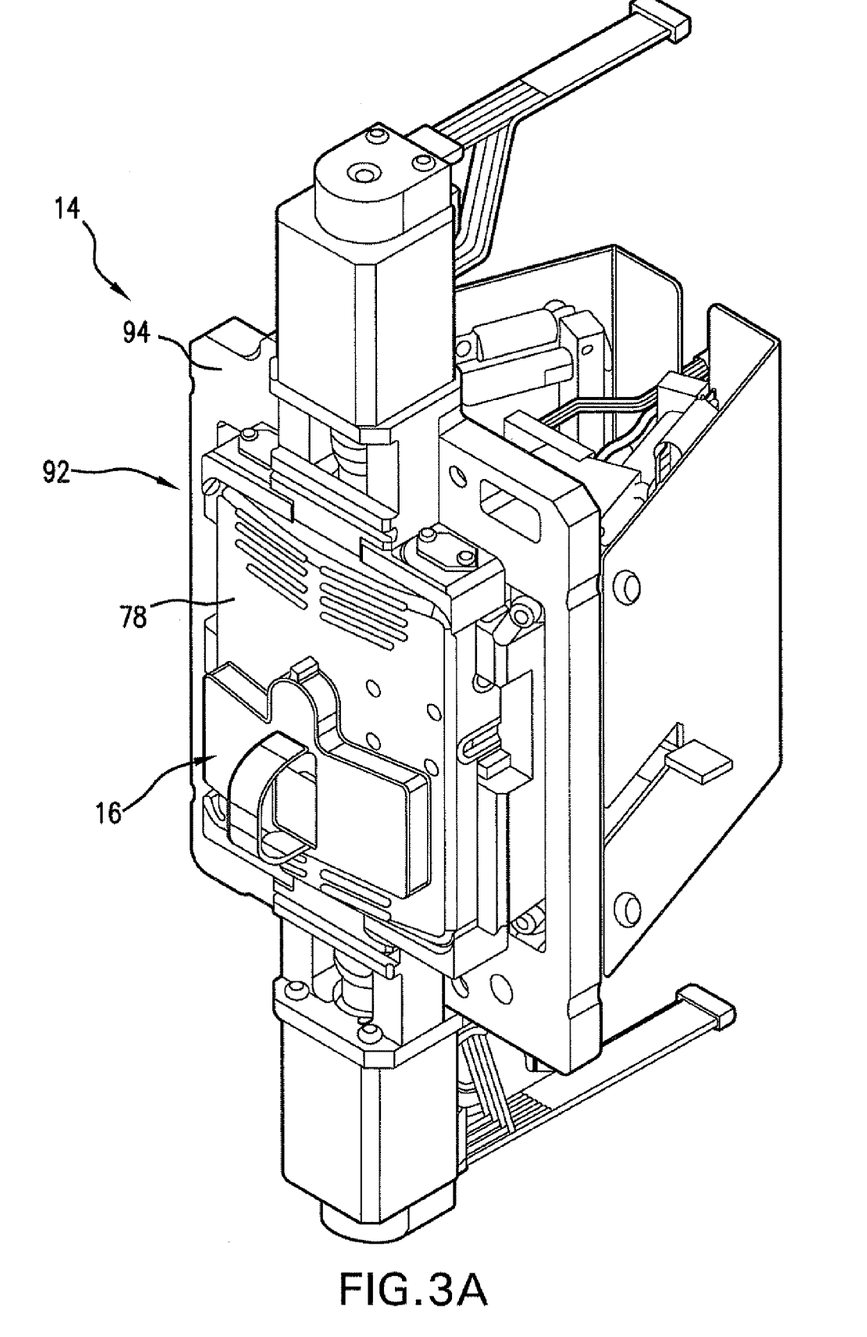
FIG. 3A is a perspective view similar to that of FIG. 3, in which the cassette is mounted to the receptacle of the console.

FIG. 3A is an illustration similar to that of FIG. 3, with cassette 16 here being fully mounted in receptacle 92 of console 14. The console includes a support structure 94 that generally supports receptacle 92, and a molded polymer cassette body 78 that generally provides support for the fluid network elements included within the cassette.

Figure 3B:
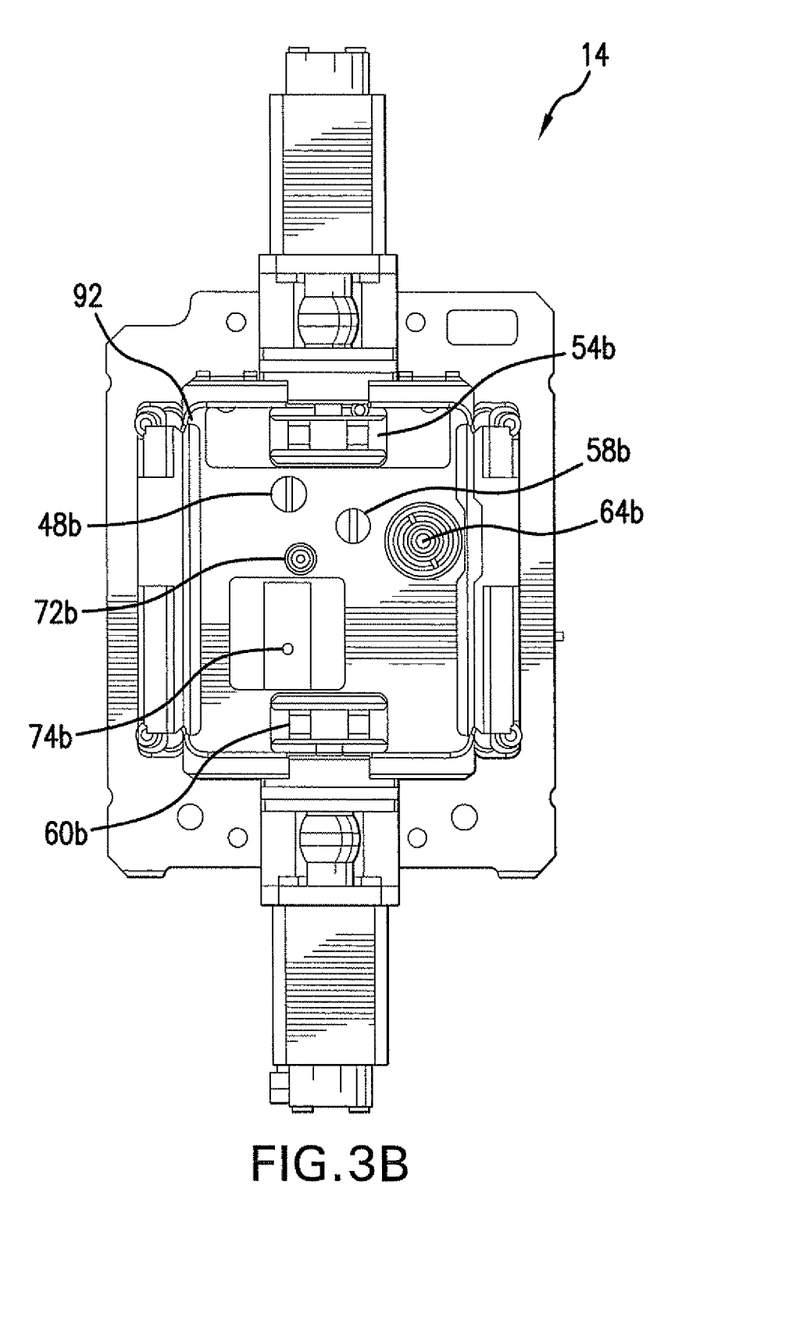
FIG. 3B is a front view showing the receptacle of the console and components of the console that interface with the cassette.

An exemplary arrangement of the console components exposed to receptacle 92 for interaction with the network elements of the cassette is shown in FIG. 3B. As mentioned above, peristaltic drive rotors 54b and 60b drive aspiration and drain pumps, respectively. An irrigation pinch valve actuator 48b moves to open or close irrigation flow through the irrigation conduit network, while a selector valve actuator 58b may be used for selecting between peristaltic pumping or vacuum pumping when cassette 16a is mounted thereon, or may be used as an irrigation vent valve 55b when cassette 16b is mounted thereon. (See FIGS. 2A and 2B) Hence, in some embodiments, actuator 58b may provide both on/off actuation and modulation of the associated flows.

A vacuum coupler 72b, preferably in the form of an axially spring-loaded nipple, provides coupling between the vacuum pump system 44 of console 14 and a vacuum coupler of holding tank 56 of the cassette. A waste fluid detector 74b may be used to identify when energizing of a drain pump 60 is appropriate.

Figure 4:
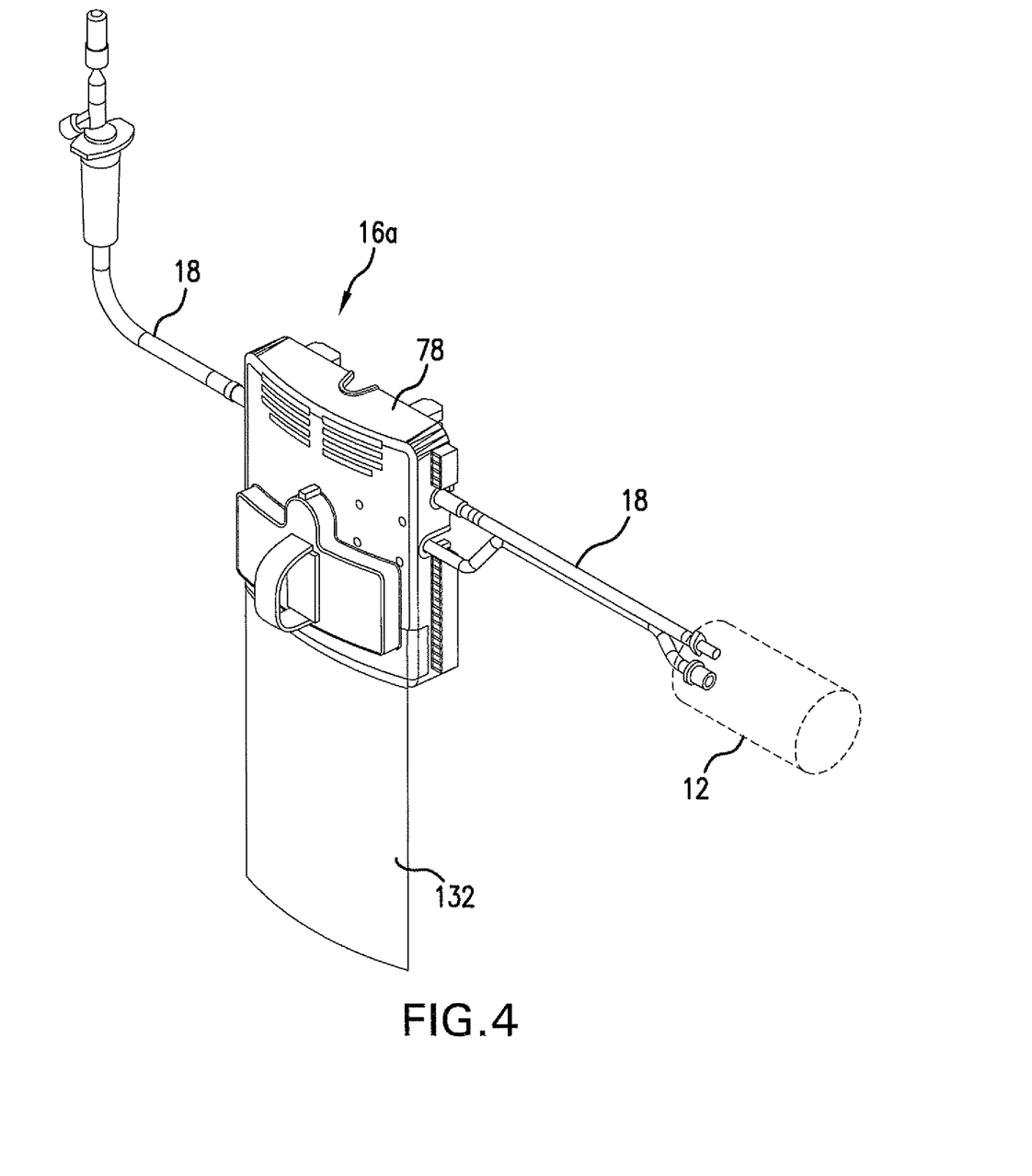
FIG. 4 is a perspective view of an exemplary surgical fluid cassette for use in the system and method of FIGS. 1 and 1A.
Figure 5A:
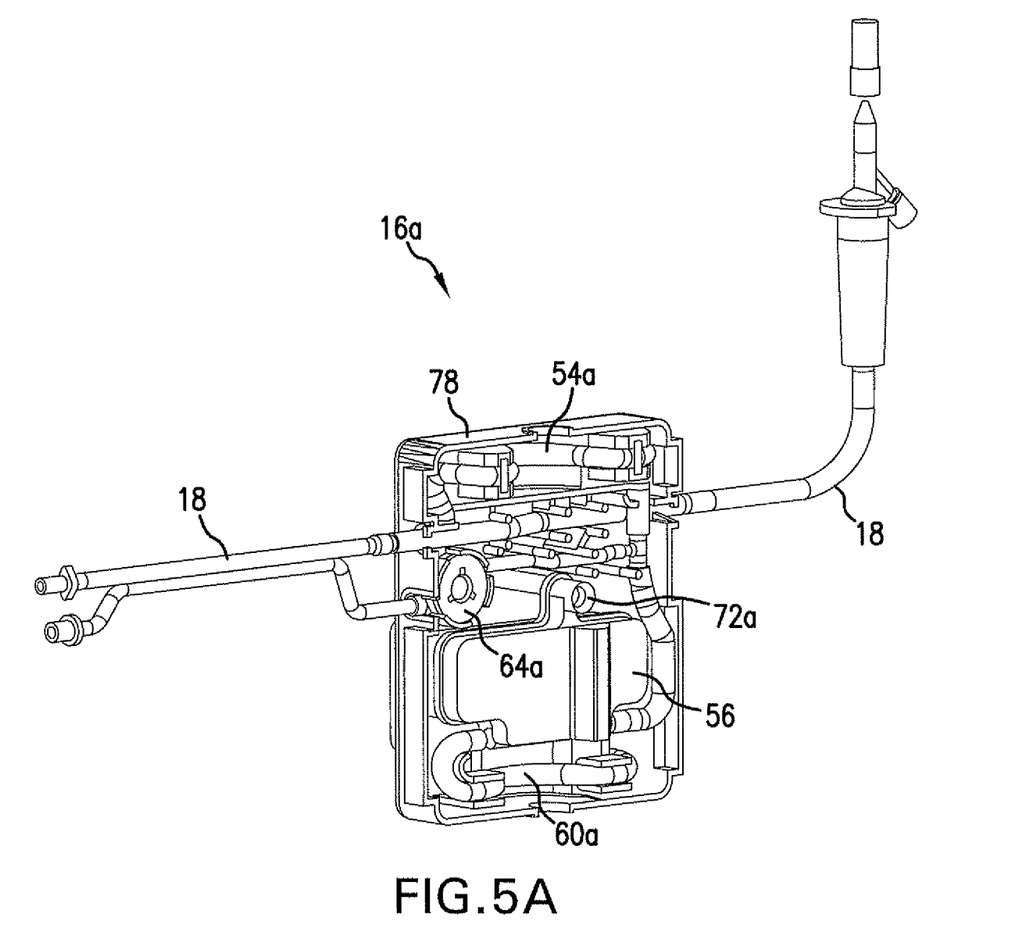
FIGS. 5A and 5B illustrate a back or interface surface of the cassette of FIG. 4 showing the fluid pathway elements assembled within the cassette body (in FIG. 5A) and in an exploded format (in FIG. 5B).
Figure 5B:
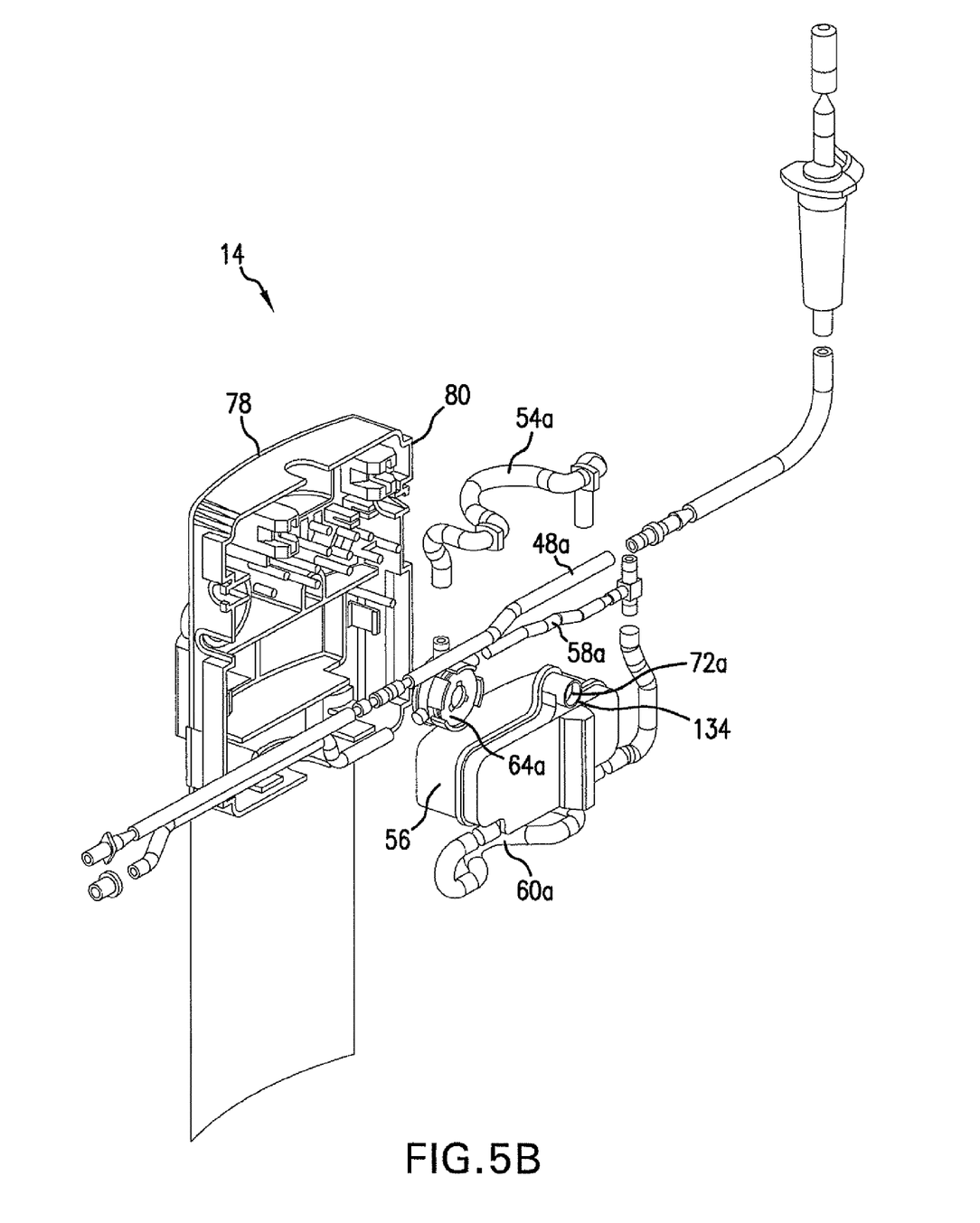

Referring now to FIGS. 4, 5A, and 5B, the structure of an exemplary cassette 16a may be better understood. Cassette 16a generally includes molded polymer cassette body 78 with the cassette body defining the positioning surfaces that engage the receptacle of the console. Flexible tubing 18 couples the cassette to an irrigation fluid supply, couples the aspiration and irrigation flow networks to the handpiece, and defines elements of the fluid networks such as pinch valves and peristaltic arc segments 54a and 60a for the aspiration pump and drain pump, respectively. The vacuum coupler 72a provides communication with holding tank 56 and interfaces with the vacuum connector of the console, while a vacuum sensor assembly 64a has a surface that deflects with changing pressure along the aspiration conduit pathway. A simple polymer fluid disposal bag 132 may be mounted to cassette body 78, with the disposal bag receiving outflow from the drain pump. The location of flexible tubing segments used for the irrigation fluid pinch valve 48a and for the selector valve 58a are seen in FIG. 5B.

Figure 6:
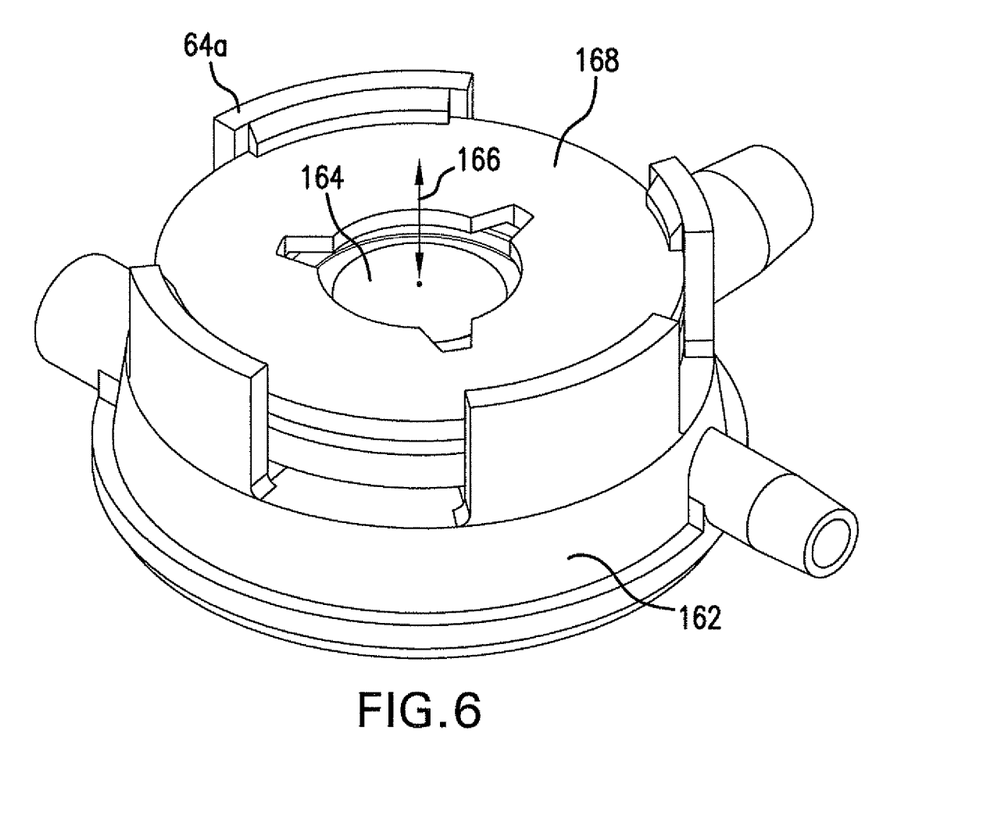
FIG. 6 is a perspective view illustrating an exemplary pressure sensor assembly of the cassette.

Sensor assembly 64a is shown in more detail in FIG. 6. A housing 162 is sealed by a displaceable surface 164, with the displaceable surface moving along an axis 166 in response to changes in pressure within the housing. A lid 168 disposed over the displaceable surface allows movement of the surface along the axis.

Figure 7A:
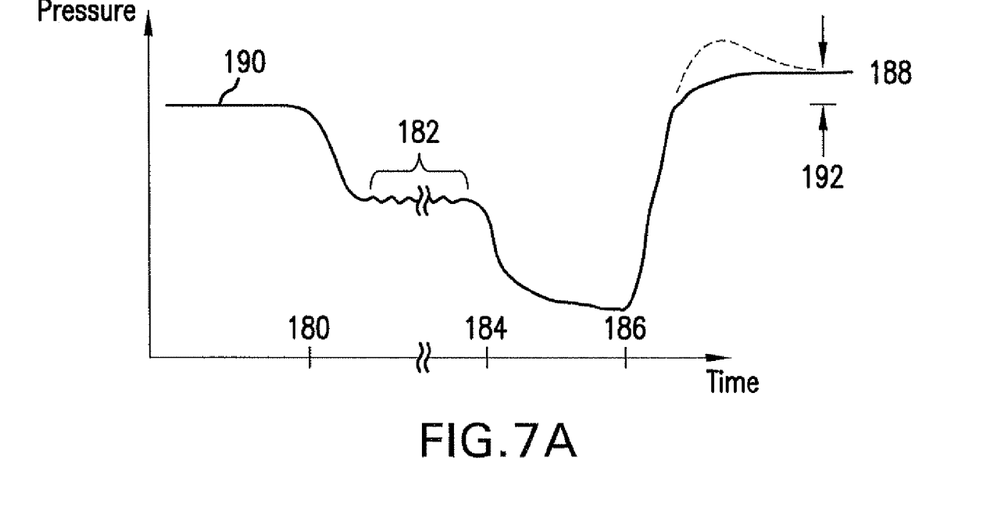
FIG. 7A graphically illustrates pressures measured by the pressure sensor of the cassette over time, showing the effects of an occlusion and reflux used to clear that occlusion.

Referring now to FIG. 7A, exemplary variations in pressure that may be measured by a pressure sensor during occlusion and venting or reflux can be understood. The pressure measured by the pressure sensor begins to change with the initiation of aspiration flow 180, with the pressure eventually reaching a substantially steady state during normal operation 182. Slight variations in pressure during this time may be encountered due to pulsation effects of the peristaltic pump, minor occlusions (which are cleared without the system or user taking action), or the like. However, a significant pressure excursion begins when the probe tip is inflicted with a hard occlusion 184 which is not quickly cleared or resolved by the ultrasound energy through the tip or the like.

The pressure excursion experienced as a result of hard occlusion 184 includes a significant decrease in the pressure measured by the sensor along the aspiration conduit pathway. To resolve the hard occlusion, the system user may input a command to the system by releasing the foot pedal, so that the foot pedal returns to its nominal or zero position (alternatively, the system may automatically initiate action based on the sensed aspiration pressure or some other system parameter). Assuming the hard occlusion is sufficient to effectively seal the aspiration port, the vent or selector valve remains closed, and the peristaltic pump is not turning (with the rotors thereby pinching the aspiration conduit pathway in a sealed configuration), the measured pressure might then remain steady (or the amount of vacuum gradually diminish and the negative pressure below atmospheric gradually increase) unless some action is taken to help remove the occluding material. Toward that end, in response to input from the system user, the peristaltic pump may be driven in a reverse direction so as to introduce fluid back into the aspiration conduit pathway between the aspiration pump and the aspiration port. Note that any driving of the aspiration pump with the foot pedal in the nominal or off position represent a departure from drive protocols of some or all standard commercial phacoemulsification systems. As described above regarding FIG. 2B, alternative systems may employ opening and/or modulation of a vent valve in response to the input command from the system user, and the input command may take a variety of different forms including actuation of a command to clear the occlusion via a keyboard, a button on the handpiece, a touchscreen interface, or the like. Regardless, fluid can be introduced into the aspiration conduit pathway between the pump and aspiration port in a controlled manner in response to the command.

Still referring to FIG. 7A, the introduction of fluid may result in a pressure 188 measured at the pressure sensor that is different than (often being slightly higher, though it may be lower in some embodiments) than a pre-aspiration pressure 190. The pressure differential 192 may compensate for differences between the height of the sensor HS and height of the eye HE, optionally as determined from the height of the tray HT as explained above regarding FIG. 1A. Nonetheless, the steady state final pressure 188 used to clear the occlusion may still result in a pressure within the aspiration conduit pathway adjacent the eye which is substantially equal to or less than the pressure of fluid within the eye or irrigation pressure adjacent the eye. Some slight pressure overshoot may occur before the steady state final pressure 188 is obtained at the sensor, although suitable reverse pumping drive characteristics and/or vent valve modulation characteristics can limit such overshoot to safe levels. In some embodiments, the system may approach the steady state pressure with the characteristics of a critically damped system, with the sensed pressure overshooting the steady state pressure a single time and then gradually approaching the steady state pressure (e.g., as illustrated by the dashed curve in FIG. 7A).

Figure 7B:
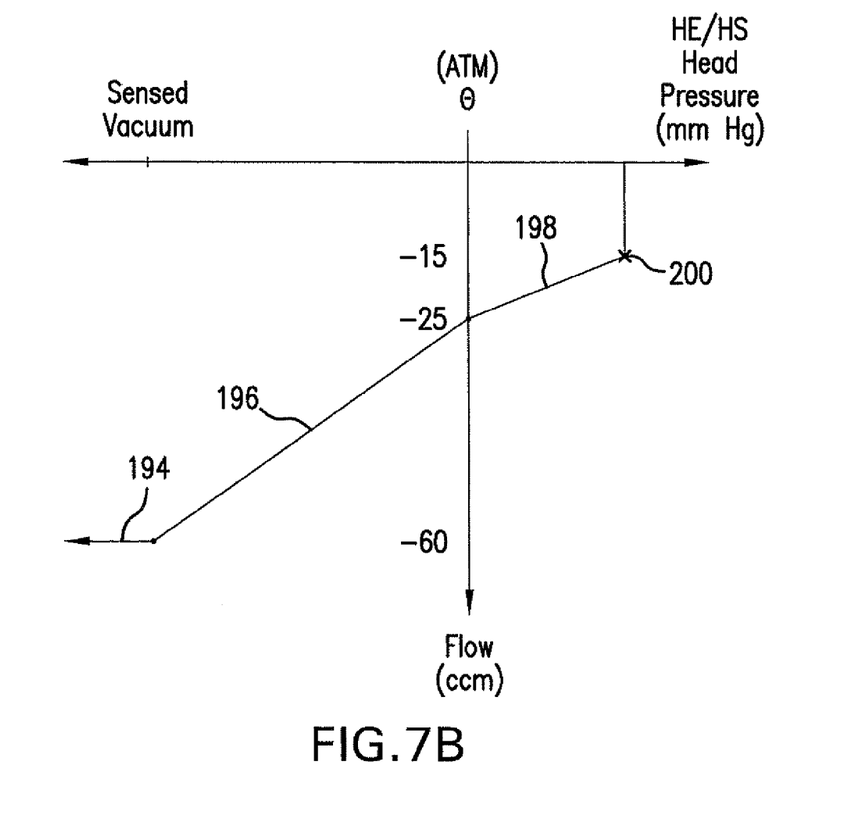
FIG. 7B graphically illustrates reverse peristaltic pump flows as determined from sensed pressure for use in the system of FIGS. 1 and 1A.

Referring now to FIG. 7B, an exemplary reverse peristaltic pump drive scheme for venting or reflux is graphically illustrated. When a command to clear an occlusion is entered by the system user, or in some embodiments, when the system processor determines the clearing of an occlusion is appropriate (such as when a reflux switch is engaged or the foot pedal returns to the nominal or off position and the pressure signal remains at a significant vacuum or negative pressure), the system processor may energize the peristaltic pump to turn in a reverse direction at a commanded speed, thereby resulting in a reverse or negative aspiration pump flow (indicated by negative cubic centimeters per minute or ccm). So long as the sensed vacuum at the sensor remains at or below negative 50 mmHg, the system controller may, for example, command the peristaltic aspiration pump to generate a negative 60 ccm aspiration flow 194. More generally, an initial reverse pumping rate may be maintained whenever sensed pressures are below a pressure in a range from about 0 mmHg to negative 650 mmHg, optionally from about negative 50 mmHg to about negative 100 mmHg, typically being from about negative 40 mmHg to about negative 80 mmHg.

Once the aspiration flow begins to moderate the level of vacuum measured by the sensor, it will often be advantageous to decrease the reverse pumping flow. For example, once the sensed negative pressure is above a threshold level of negative 50 mmHg, the processor may determine an appropriate reverse pumping flow rate (or alternatively pump speed) from a linear correlation 196 between the sensed vacuum and the flow rate (or alternatively pump speed). An exemplary correlation provides a linear relationship throughout the range of 50 mmHg of negative pressure to 0.0 mmHg or atmospheric pressure.

To avoid excessive overshoot in the pressure or overpressurization of the eye, the overall correlation between reverse pumping flow rate and sensed negative pressure may include a second correlation portion 198 having a different (and often smaller) slope once the pressure within the aspiration conduit pathway adjacent the eye approaches the internal pressure of the eye and/or irrigation fluid pressure at the eye. In the exemplary system, the system processor linearly decreases the reverse pumping flow rate from negative 25 ccm to negative 15 ccm as the sensed pressure varies between atmospheric and the stopping point. The slope of the linear correlation 196 may vary. For example, the flow rate when the sensed pressure reaches atmospheric pressure may be anywhere from about zero ccm to a flow rate that is at or about equal to the flow rate when the pump begins to slow down (negative 60 ccm in the present embodiment). In some embodiments, the second linear correlation 198 is initiated either before or after the sensed pressure is equal to atmospheric.

Reverse pumping of the aspiration flow pump may be halted once the signals from the aspiration vacuum sensor indicate that the pressure within the aspiration conduit pathway adjacent the eye is equal to or near the irrigation fluid pressure adjacent the eye. The calculations to determine the halting point can be understood with the description above of FIG. 1A. If the halting pressure has not been reached within some appropriate predetermined time range of initiation of reverse pumping, such as within about 3 seconds of initiation of reverse pumping, reverse pumping may be halted before the target pressure has been reached. Note that the target termination pressure 200 in the illustrated embodiment may vary depending on the height of the eye (optionally as determined from the height of the tray), the height of the fluid supply for the irrigation fluid, and the like. Hence, the slope of the correlation 198 may also vary for different patients, surgeon preferences, or procedure types. Regardless, the flow rate will generally go to zero once the sensed pressure is equal to or greater than a predetermined end point pressure, or when the time limit for reverse pumping has been reached.

The exemplary overall correlation between sensed pressure and reverse pumping flow rate illustrated in FIG. 7B generally includes three pressure ranges or correlation portions 194, 196, and 198, with the slope of the correlation differing between these different ranges. Alternative embodiments may employ more than three ranges or less than three ranges, and/or may employ non-linear relationships between the pressures and flow.

While the exemplary embodiments have been described in some detail for clarity of understanding and by way of example, a variety of modifications, changes, and adaptations will be clear to those of skill in the art. Hence, the scope of the present invention is limited solely by the appended claims.

What is claimed is:

1. An eye treatment method comprising: providing a phacoemulsification system comprising
   an irrigation conduit pathway,
   an aspiration pathway,
   a pump, wherein the pump is coupled with the aspiration pathway, and
   a pressure sensor, wherein the pressure sensor is coupled with the aspiration pathway;
   directing an irrigation flow into the eye through the irrigation conduit pathway;
   aspirating material from within the eye by drawing an aspiration flow through the aspiration conduit pathway with the pump; and
   sensing a pressure via the pressure sensor indicating pressure within the aspiration conduit pathway;
   providing a first correlation between the sensed pressure and a reverse pump speed, or between the sensed pressure and a reverse flow rate;
   providing a second correlation between the sensed pressure and the reverse pump speed, or between the sensed pressure and the reverse flow rate;
   reversing the pump to provide an initial reverse flow rate;
   based on the sensed pressure, selecting the first correlation or the second correlation, the sensed pressure being within a predetermined pressure range;
   and based on the selection, controlling the reverse pumping flow rate.

2. The method of claim 1, wherein the pump comprises a volumetric pump, wherein an occlusion induces a complaint reduction in volume of the aspiration conduit between the eye and the pump, and wherein the reversing of the pump at least partially compensates for the reduction in volume.

3. The method of claim 2, further comprising controlling the reversing of the pump in response to an aspiration system parameter.

4. The method of claim 3, wherein the reversing of the pump is halted when the sensed pressure is less than or substantially equal to an irrigation flow pressure at the eye so that the reflux into the eye is largely generated by momentum in the aspiration conduit pathway toward the eye.

5. The method of claim 2, wherein a substantially constant reverse pumping flow rate is maintained while the sensed pressure comprises a vacuum above a vacuum threshold.

6. The method of claim 2, wherein a reduced reverse pumping flow rate is determined from the sensed pressure is between a vacuum threshold and atmospheric pressure, the reduced reverse pumping flow rate decreasing linearly with decreasing vacuum.

7. The method of claim 6, wherein the reduced reverse pumping flow rate is determined from the sensed pressure that is more than atmospheric pressure and while a pressure of the aspiration flow adjacent the eye is less than an irrigation pressure at the eye, the reduced reverse pumping flow rate decreasing linearly with increasing pressure.

8. The method of claim 1, wherein the irrigation and aspiration flows are initiated by actuation of a foot pedal input device from a nominal undeflected position to a first position, and from the first position to the second position, respectively, and wherein the pump is reversed while the foot pedal input device is released back to the nominal position.

9. The method of claim 1, further comprising controlling the reversing of the pump in response to a pressure of the irrigation flow and a height of the eye of the patient.

10. The method of claim 9, wherein the height of the eye of the patient is estimated from a height of an accessory tray of the system.

11. The method of claim 1, wherein a vacuum source is coupled to the aspiration fluid conduit by an aspiration selector valve, and further comprising closing the aspiration selector valve during the aspiration of material and reversing of the pump.

12. The method of claim 1, wherein the first correlation and the second correlation are each linear correlations, the second correlation having a slope that is different from the first correlation.

* * * * *